United States Patent
Chan et al.

(10) Patent No.: US 6,638,205 B1
(45) Date of Patent: Oct. 28, 2003

(54) RADIOACTIVE MEDICAL DEVICE FOR RADIATION THERAPY

(75) Inventors: Albert Chan, Ottawa (CA); Corinne Bensimon, Kanata (CA)

(73) Assignee: MDS (Canada) Inc., Ottawa (CA)

( * ) Notice: Subject to any disclaimer, the term of this patent is extended or adjusted under 35 U.S.C. 154(b) by 0 days.

(21) Appl. No.: 09/716,177

(22) Filed: Nov. 17, 2000

(51) Int. Cl.⁷ .............................. A61N 5/00; B23P 25/00
(52) U.S. Cl. .............................................. 600/3; 29/458
(58) Field of Search ........................ 600/3, 7; 623/1.13; 606/189; 29/458

(56) References Cited

U.S. PATENT DOCUMENTS

| | | | |
|---|---|---|---|
| 3,351,049 A | 11/1967 | Lawrence | 128/1.2 |
| 3,811,426 A | 5/1974 | Culver et al. | 128/1.2 |
| 4,323,055 A | 4/1982 | Kubiatowicz | 128/1.2 |
| 4,508,119 A * | 4/1985 | Tukamoto | 606/189 |
| 5,163,896 A | 11/1992 | Suthanthiran et al. | 600/8 |
| 5,342,283 A | 8/1994 | Good | 600/8 |
| 5,405,309 A | 4/1995 | Carden, Jr. | 600/3 |
| 5,713,828 A * | 2/1998 | Coniglione | 600/7 |
| 5,871,436 A * | 2/1999 | Eury | 600/3 |
| 5,873,904 A * | 2/1999 | Ragheb et al. | 623/1.13 |
| 5,924,973 A * | 7/1999 | Weinberger | 600/3 |
| 5,938,604 A | 8/1999 | Wagner et al. | 600/436 |
| 6,010,445 A * | 1/2000 | Armini et al. | 600/3 |
| 6,163,947 A * | 12/2000 | Coniglione | 29/458 |
| 6,254,552 B1 * | 7/2001 | Lewis et al. | 600/603 |

FOREIGN PATENT DOCUMENTS

| | | | | |
|---|---|---|---|---|
| CA | 2010038 | | 8/1990 | |
| WO | WO 99/17812 | * | 4/1999 | ... A61K/51/12 |

OTHER PUBLICATIONS

Blair, A., "Silver Plating," Surface Engineering, The Materials Information Society, ASM International, vol. 5, pp. 245–246(1996).

Raub, Ch. J., "Platinum–Group Metals Plating," Surface Engineering, The Materials Information Society, ASM International, vol. 5, pp. 251–252 (1996).

* cited by examiner

Primary Examiner—Eric F. Winakur
Assistant Examiner—Nikita R Veniaminov
(74) Attorney, Agent, or Firm—Heslin Rothenberg Farley & Mesiti P.C.

(57) ABSTRACT

The present invention discloses a radioactive medical device comprising a radioactive, electroplated substrate coated with at least one layer of polymer and sealed in a jacket layer. The at least one layer of polymer and jacket layer reduce leaching of a radioactive element from the electroplated substrate. The radioactive medical device is useful for radiation therapy of diseased tissue such as cancers and especially malignant tumors.

20 Claims, 6 Drawing Sheets

RADIOACTIVE MEDICAL DEVICE FOR RADIATION THERAPY

The invention relates to radioactive medical devices. More specifically, the invention relates to radioactive medical devices which may be used in radiation therapy of diseased tissue.

BACKGROUND OF THE INVENTION

Radiation therapy is used extensively to treat diseased tissue such as cancers and especially malignant tumors. The goal of radiation therapy is to destroy the diseased or malignant tissue without causing excessive damage to nearby healthy tissue. One form of radiation therapy involves directing one or more beams of radiation from a point external to a subject's body into the area in which the tumor, malignant cells or diseased tissue, is located. Unfortunately, the beam of radiation must pass through healthy tissue to reach the diseased target tissue.

Another type of radiation therapy involves the delivery of a radioactive source directly to the site of diseased tissue. These methods include, for example, the use of a catheter, the surgical implantation of one or more radioactive seeds, or the injection of one or more seeds into the patient in close proximity to the diseased tissue.

Prior art radioactive sources typically have a radioactive element affixed to a substrate, and the radioactive substrate covered with a bio-compatible sealing layer to prevent leaching of the radioactive element into the patient. For example, U.S. Pat. No. 5,938,604 discloses a needle comprising an electroplated radioactive metal (Tc99m) that is covered with additional layers of plating to prevent subsequent removal of the radioactive material. Similarly, U.S. Pat. No. 5,405,309 teaches electroplating a Palladium-103/Palladium admixture onto a pellet of electroconductive material and further electroplating the pellet with a bio-compatible container or shell, such as titanium. A major limitation of the teachings of these patents is that the outer plating layers absorb a significant amount of radiation emitted from the radioactive inner plating layer requiring that high levels of radioactivity must be deposited on the inner layer to compensate for the radiation attenuation by the outer plating layer. The deposition of higher levels of radioactivity on the inner plating layer is costly. Further, the substrates are electroplated first with a radioactive element and then electroplated again or sealed within a bio-compatible container or shell. These methods are complex and expensive, and introduce the possibility of increasing the risk to workers during the second electroplating step.

U.S. Pat. No. 4,323,055 to Kubiatowicz, discloses that chemisorbtion of I-125 onto a silver layer, and these coated seeds are then sealed within a titanium container in order to effectively control the migration of I-125 from the seed. However, the use of a titanium outer shell results in substantial attenuation of the outer protective layer. U.S. Pat. No. 4,323,055 discloses radioactive seeds for use in radiation therapy of diseased tissue. The seed comprises a sealed container having a therapeutic amount of radioactive iodine distributed on a carrier body. The carrier body is disposed in a cavity of a tubular titanium container which is sealed at both ends. Radioactive iodine is attached to a silver substrate by first chloriding or bromiding the silver to form a layer of insoluble silver chloride or silver bromide and then replacing the chloride or bromide ions by simple ion exchange. Unfortunately, the level of radioactivity incorporated must be increased to compensate for the 14% attenuation in the radiation field by the titanium container. The incorporation of increased levels of radioactivity to compensate for the attenuation by the container is costly. U.S. Pat. No. 3,351,049 also relates to radioactive seeds comprising a central body coated with a radioisotope that is sealed in a container. In one embodiment, the container is constructed of a metal of a low atomic number, such as stainless steel alloy or titanium. However, as disclosed within the patent, the attenuation of stainless steel is about 15% per thousandth of an inch while the attenuation for titanium is about 5% per thousandth of an inch, and additional radioisotope must be added to compensate for absorption losses in the container walls. It is noted that I-125 seeds require a metallic seal to prevent leaching of I-125 from the substrate, again significantly attenuating the amount of radiation emmnited from the seed. An analogous approach is disclosed in U.S. Pat. No. 3,811,426 that comprises depositing Pu-238 onto a wire. The radioisotope layer is covered with a coating layer such as platinum. Both the radioactive layer and the coating layer are applied by electrolytic processes such as sputter deposition. Again, the coating layer attenuates the radiation emitted by the radioactive layer of the wire. Also, the two electroplating processes make the radioactive wire more difficult and more expensive to make than radioactive wires comprising a single electroplating step and an easy and inexpensive coating step. Furthermore, wires that are electroplated or electrosputtered exhibit little or no flexibility.

U.S. Pat. No. 5,713,828 discloses a brachytherapy device formed from a hollow, tube-shaped substrate on which a radioactive source is disposed. The radioactive seed is sealed in a sealing layer comprising an organic coating such as polypropylene, polyethylene terephthalate, nylon, polyurethane or a bio-compatible metal or metal compound. The disclosed brachytherapy device must be of dimensions which allows a support material such as a surgical thread to be threaded through the hollow tube of the device. Thus the brachytherapy device is limited as to its minimum diameter. Further, it is well known in the art that certain radioactive elements such as iodine are not easily retained on substrates because of their volatility. The above-identified patent contemplates coating substrates with iodine-125 according to the chemisorbtion method disclosed in U.S. Pat. No. 4,323,055 (Kubiatoicz), however, an I-125 coated substrate sealed in a single sealing layer as taught in U.S. Pat. No. 5,713,828 may allow leaching of significant amounts of radioactive I-125 within a patient. Since it is well known that iodine accumulates in the thyroid gland in humans, the smallest amount of I-125 leaching from the disclosed brachytherapy device could severely compromise the health of a patient. A similar method is disclosed in U.S. Pat. No. 5,163,896 which comprises coating a tungsten rod or pellet with a radioactive-absorbing binder material to which a radioactive material is adsorbed. The radioactive rod is encapsulated with a coating material which seals the pellet. The pellet may be encapsulated in a container made of material other than titanium provided that the container material does not substantially inhibit irradiation from the seed, and provided that the material is resistant to corrosion by body fluids. This method is generally not applicable with the use of volatile radioactive elements such as I-125 which would leach from the binder material over prolonged periods.

U.S. Pat. No. 5,342,283 (Good) relates to radioactive implants and a method for making radioactive implants. The patent teaches incorporating a radioactive element into a seed, ribbon or wire, and subsequently coating the radioactive layer with other coating layers comprising a metal diffusion barrier (for example titanium, tantalum, gold, platinum, tungsten carbide) and a bio-compatible protective coat including metal (e.g. titanium), or diamond or diamond-like carbon. The diffusion barrier and protective coat are deposited on the radioactively coated substrate by sputtering, laser-ablation ion plating, or cathodic arc plasma deposition. The diffusion barrier and the protective coat may absorb significant amounts of radiation emitted from the radioactive inner plating layer and therefore high levels of radioactivity must be deposited prior to being coated with the diffusion and outer plating layers, which is costly. Thus, these implants are more difficult and costly to produce than implants which require a single electroplating step and an easy and inexpensive coating step for their manufacture.

Canadian patent application CA 2,010,038 relates to production and use of Yb-168 or Yb-169 seeds and wires via neutron bombardment. These radioactive substrates may comprise an outer coating of titanium, aluminum, PTFE-coated aluminum or other plastic. There is no disclosure of seeds comprising other isotopes.

There is a need in the art for radioactive, electroplated substrates of high activity and substantially uniform radioactivity that are both easy and inexpensive to manufacture. Further, there is a need for radioactive, electroplated substrates that are coated and sealed with layers of material that reduce leaching of the radioactive element from the substrate, yet are minimize attenuation of the radiation so that the layers of material do not substantially absorb the radiation emitted from the substrate. There is also a need for radioactive substrates having coating or sealing layers which do not impart excessive bulk to the radioactive substrate or alter the tensile properties, such as pliablility or malleability of the substrate.

It is an object of the present invention to overcome drawbacks of the prior art.

The above object is met by a combination of the features of the main claims. The sub claims disclose further advantageous embodiments of the invention.

SUMMARY OF THE INVENTION

The present invention relates to radioactive medical devices. More specifically, the invention relates to radioactive medical devices useful for radiation therapy of diseased tissue.

According to the present invention, there is provided a radioactive medical device comprising a radioactive, electroplated substrate coated with at least one layer of polymer and sealed in a jacket layer.

The present invention also relates to a radioactive medical device as described above wherein the substrate is formed entirely of metal, or partially of a metal. The substrate may be silver and have the shape of a wire. The radioactive medical device may be a stent, wire or a seed.

The present invention also relates to radioactive medical devices as described above electroplated with a radioactive element that may be selected from the group consisting of P-32, S-35, Cl-36, Sc-47, Cu-67, Y-90, Mo-99, Pd-103, Sn-117m, I-123, I-124, I-125, I-129, -131, Ce-144, Ho-166, Re-186, Re-188, W-188, Ir-192, and Au-199.

The present invention also relates radioactive medical devices as described above having from 1 to about 10 layers of polymer. The polymer may be selected from the group consisting of polyurethane polypropylene, polysulfone, polyphenylsulfone, polyethersulfone, polyimide, VITON, nylon, polyester/polyolefins, ceramics, PVP, cellulose.

The present invention also relates to a method of manufacturing a radioactive medical device coated with at least one layer of polymer and sealed in a jacket layer, comprising the steps of;

a) electroplating a substrate with a radioactive element to form a radioactive, electroplated substrate;

b) coating the radioactive-electroplated substrate in at least one layer of polymer to form a radioactive, electroplated substrate coated with at least one layer of polymer and;

c) sealing the radioactive, electroplated substrate coated with at least one layer of polymer in a jacket layer.

The present invention also relates to the use of the radioactive medical device as defined above for delivery of radiation to diseased tissue. Further, the radioactive medical device may be used for brachytherapy or for restenosis.

This summary does not necessarily describe all necessary features of the invention but that the invention may also reside in a sub-combination of the described features.

BRIEF DESCRIPTION OF THE DRAWINGS

These and other features of the invention will become more apparent from the following description in which reference is made to the appended drawings wherein:

FIG. 1 shows an aspect of an embodiment of the present invention comprising a radioactive electroplated substrate coated with a layer of polymer and sealed in a jacket layer.

FIG. 2 shows various aspects of embodiments of the present invention.

FIG. 5A shows the radioactivity distributed along one side of the radioactive medical device of the present invention following a five minute film irradiation period. FIG. 5B shows the radioactivity distributed along the side opposite that imaged in FIG. 5A during the same 5 minute irradiation period. FIG. 5C shows the radioactivity distributed along one side of the radioactive medical device of the present invention following a ten minute film irradiation period. FIG. 5D shows the radioactivity distributed along the side opposite that imaged in FIG. 5C during the same ten minute irradiation period.

DESCRIPTION OF PREFERRED EMBODIMENT

The present invention relates to radioactive medical devices. More specifically, the invention relates to radioactive medical devices useful for radiation therapy of diseased tissue.

Figure 1A:
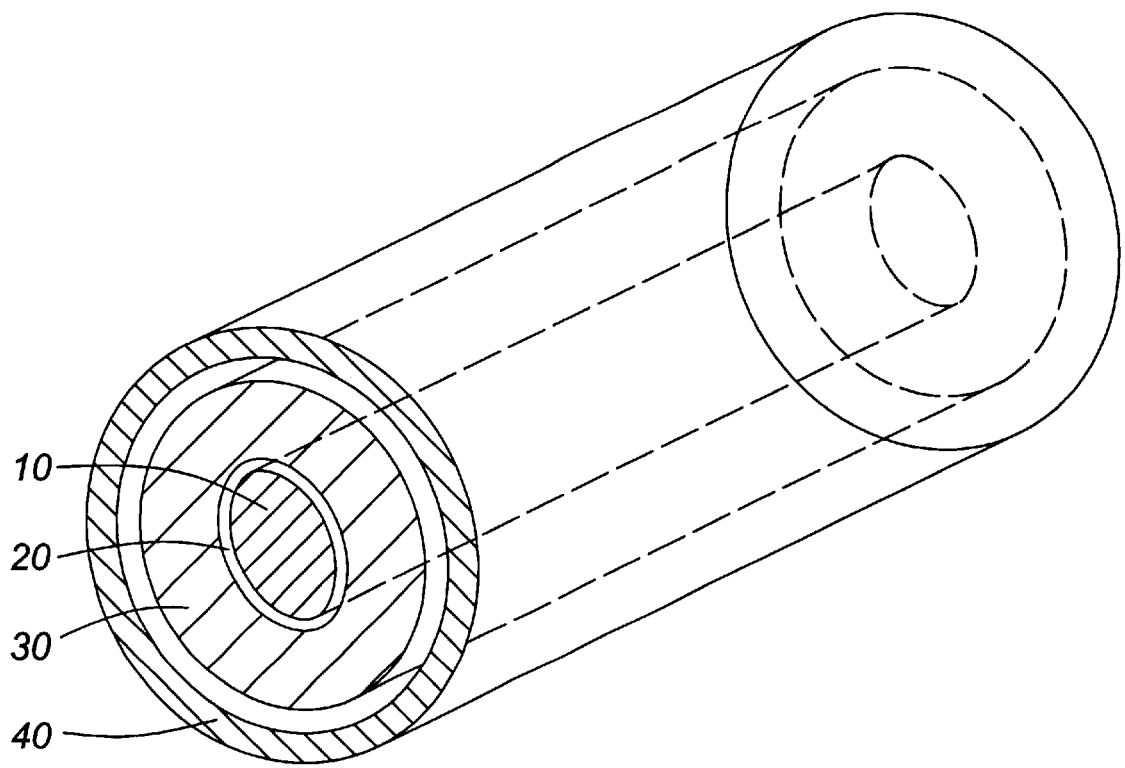
FIG. 1(A) shows a perspective view of a coated substrate.
Figure 1B:
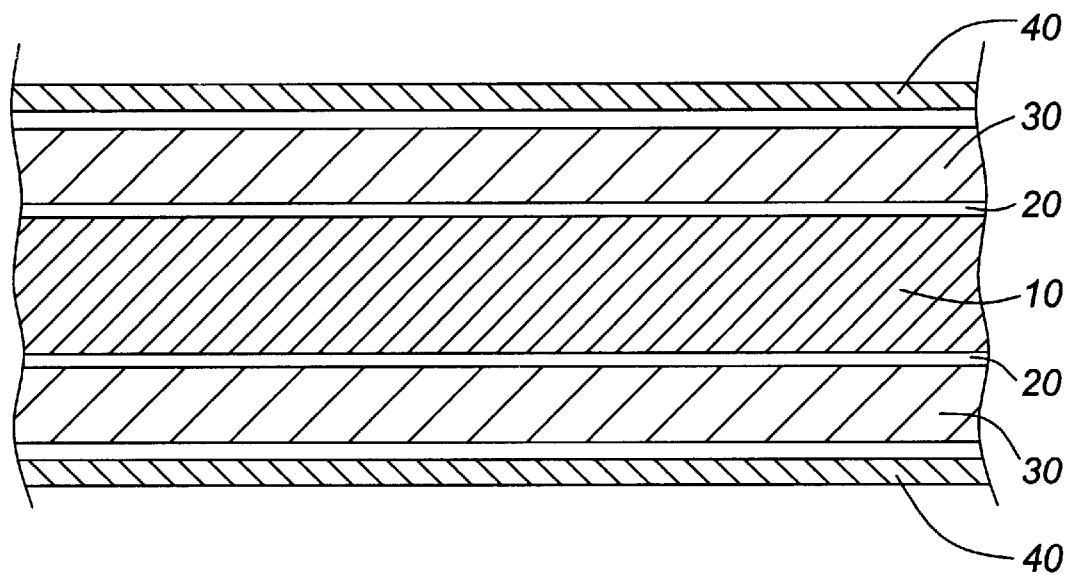
FIG. 1(B) shows a longitudinal section of a coated substrate.
Figure 2A:
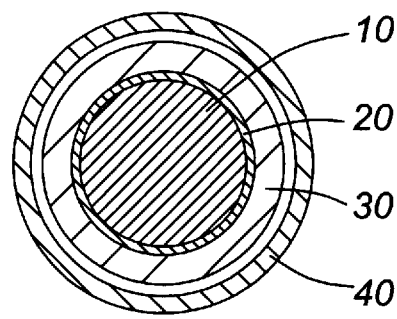
FIG. 2A shows a substrate comprising a radioactive layer, coated with a single layer of polymer and sealed in jacket layer.
Figure 2B:
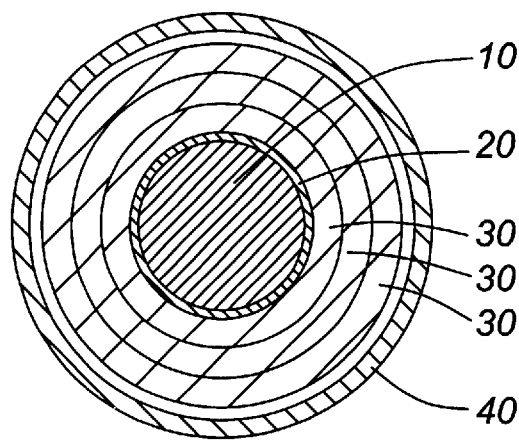
FIG. 2B shows a substrate comprising a radioactive layer, coated with multiple, identical layers of polymer and sealed in jacket layer.
Figure 2C:
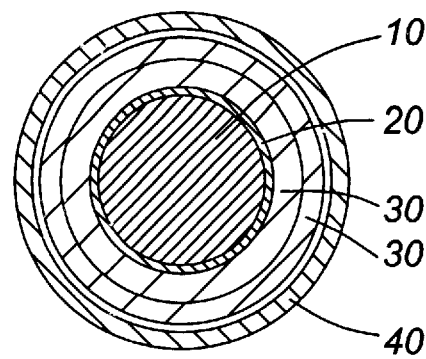
FIG. 2C shows a substrate comprising a radioactive layer, coated with multiple layers of polymer and sealed in jacket layer. The multiple layers of polymer are of different thicknesses.
Figure 2D:
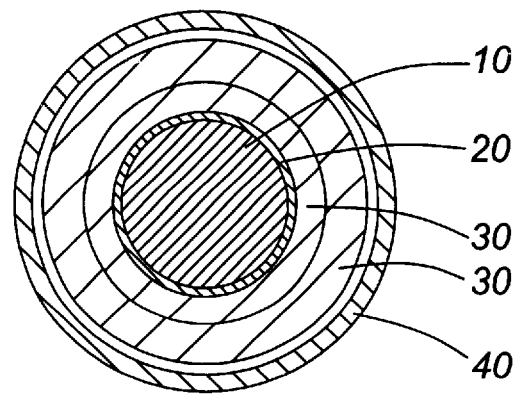
FIG. 2D shows a substrate comprising a radioactive layer, coated with multiple layers of polymer and sealed in jacket layer. Each layer of the multiple layer of polymer is of a different composition and thickness.

According to the present invention, there is provided a radioactive medical device comprising a radioactive, electroplated substrate that is coated with a polymer layer and this polymer coated substrate is then sealed in an outer jacket layer. Referring now to FIG. 1, which depicts an aspect of an embodiment of the present invention, the radioactive, electroplated substrate comprises a substrate (10) and a radioactive layer (20) deposited thereon by an electroplating process. The radioactive, electroplated substrate is coated with a polymer coating (30) and sealed in an outer jacket layer (40).

The radioactive, electroplated substrate of the radioactive medical device of the present invention may comprise any substrate which can be electroplated with a desired radioactive element. The substrate may comprise a solid metal object made from a single metal or the substrate may comprise a metal object made from a plurality of metals. Alternatively, the substrate may comprise metal and non-metal portions, for example, but without wishing to be limiting, the substrate may comprise a non-metal portion which is coated, or encapsulated with a metal or a plurality of metals. The substrate of the radioactive medical device of the present invention may be of any shape or of variable dimension. For example, but without wishing to be limiting, the substrate may comprise a ribbon, wire, disk, seed, tube or a combination thereof. Examples of metallic substrate that may be coated with a radioactive isotope of interest by electroplating include but are not limited to, silver, bronze, stainless steel, nitinol (nickel titanium alloy), zirconium, aluminum, brass, zinc, titanium, platinum, tantalum, rohdium and palladium. The amount of activity loaded onto the substrate can be varied through the process reaction time and the specific activity of the isotope.

The radioactive element which is to be electroplated onto the substrate may comprise any radioactive element, or a combination of radioactive elements, capable of being electroplated. Examples of radioactive elements which may be electroplated include, but are not limited to P-32, S-35, Cl-36, Sc-47, Cu-67, Y-90, Mo-99, Pd-103, Sn-117m, I-123, I-124, I-125, I-129, I-131, Ce-144, Ho-166, Re-186, Re-188, W-188, Ir-192, and Au-199.

The electroplating method of affixing radioisotopes onto a non-radioactive substrate is designed to achieve a uniform coverage of the substrate resulting in a predictable radiation field at a given distance from the device. The electroplating procedure utilizes an aqueous solution of a salt compatible with the isotope to be plated onto the substrate. General procedures relating to electroplating are well known within the art (e.g. ASM Handbook, Surface Engineering, Vol 5, 1990, ASM International, which is incorporated herein by reference). For example, but not to be considered limiting, NaI, or KI may be used with I-125 or related isotopes, or $PdCl_2$ with Pd-103. The metallic substrate to be coated may be used as the anode or cathode as required depending upon the charge of the isotope to be plated For example, but not to be considered limiting, for the plating of I-125, a silver wire may be used as an anode along with a platinum wire is used as the cathode. In this combination of electrodes, platinum acts as an inert conductor, in that it does not participate in the redox chemistry, except as a conductor of electrons for other chemical reaction to occur. Other metals may be used as anode or cathodes as would be evident to one of skill in the art, for example, but not limited to palladium, rhodium, ruthenium, osmium, platinum, iridium (e.g. Raub Ch. J 1990, ASM Handbook, pp. 251–254, which is incorporated herein by reference), or silver (Blair A, 1990 ASM Handbook, pp. 245–246, which is incorporated herein by reference).

Following electroplating, the radioactive substrate is first coated with at least one layer of a polymer. The polymer may comprise any polymer known in the art. For example, but not wishing to be limiting, the polymer may comprise polyurethane, polypropylene, polysulfone, polyphenylsulfone, polyethersulfone, polyimide, viton, nylon, polyester/polyolefins, ceramics, PVP, cellulose ester, polyglycolide, polylactic, nylon 6/6, polyethylene glycol, polyvinylidene fluoride, epoxy, or a combination thereof. Preferably the polymer layer is polyurethane, for example but not limited to, polyurethane EG-65D. For embodiments of the present invention in which the radioactive, electroplated substrate is first coated with a plurality of layers of polymer and second, is sealed in a jacket layer, the layers of polymer comprising the first polymer coating may be similar or dissimilar in composition and physical characteristics, providing that each polymer layer is compatible with the previous or subsequent polymer layer. Further, the one or more layers of polymer may comprise other chemicals or additives such as, but not limited to stabilizers, epoxy, and polyvinylidene fluoride.

Each layer of the first polymer coating may be applied onto the electroplated substrate of the present invention using any method evident to someone of skill in the art. For example, each polymer layer may be applied to the radioactive, electroplated substrate as a liquid, for example, but not limited to, by dipping the radioactive, electroplated substrate into a solution comprising polymer and a suitable solvent. The polymer may also be sprayed or painted etc, onto the radioactive substrate. Between polymer layers, the polymer may be permitted to partially or completely dry as needed. The polymer or polymer solution may be heated to produce a homogeneous solution or reduce the viscosity of the polymer solution, as is known in the art. Also, by varying the ratio of the mass of polymer to the mass of solvent, it is possible to prepare polymer solutions having different mass fractions of polymer and solvent and therefore different viscosities. Without wishing to be bound by theory, by varying the viscosity of the polymer solution, the thickness of the coating of each layer of polymer of the radioactive medical device may be controlled. For example, a polymer solution comprising a relatively high mass ratio of polymer to solvent may provide a thicker polymer coating upon dipping or spraying than a polymer solution comprising a relatively low mass ratio of polymer to solvent, under identical conditions. However, without wishing to be limiting, the thickness of each polymer layer may be affected by type and the amount of the polymer or polymers in solution, the amount and properties of the solvent if present, the temperature of the polymer, the nature of the dipping, spraying or other coating procedure, or combinations thereof. Since each layer of polymer of the radioactive medical device of the current invention may be applied as a liquid, someone of skill in the art will understand that in embodiments directed to coating with a plurality of layers of polymer, the individual coats or layers of polymer may be indistinguishable from one another, especially in embodiments wherein the radioactive, electroplated substrate is coated with multiple, identical layers of polymer. If more than one layer is applied, then the solvent may dissolve or solvates the previous polymer layer such that a homogeneous, continuous polymer coating may be obtained.

Referring now to FIG. 2 there are shown multiple aspects of embodiments contemplated by the present invention. FIG. 2A depicts a substrate (10) comprising a radioactive layer (20) deposited thereon by an electroplating process, coated with a single layer of polymer (30) and sealed in a jacket layer (40). FIGS. 2B–D depict a substrate (10) comprising a radioactive layer (20) deposited thereon by an electroplating process, coated with at least one layer of polymer (30) and sealed in a jacket layer (40). In the aspect of the embodiment shown in FIG. 2B, each layer of the polymer coating is identical. In FIG. 2C, each layer of the polymer coating comprises the same polymer, but the thickness of each layer of the polymer coating is different. In the aspect of the embodiment shown in FIG. 2D, each polymer layer is different in both composition and thickness.

It is preferable that the coating of the polymer layer does not significantly alter the properties of the substrate. For example, but not wishing to be limiting, a pliable substrate should remain pliable following electroplating and coating with a polymer layer. Furthermore, it is preferable that coating the radioactive, electroplated substrate with the polymer is easy to perform and relatively inexpensive.

The polymer layer protects the radioactive, electroplated substrate and acts as a barrier to reduce, or substantially reduce leaching of the radioactive element from the radioactive, electroplated substrate. Furthermore, the polymer layer is transparent with respect to the emitted radiation and attenuation of the radiation by this layer is negligible. It is not necessary that the polymer layer completely block or stop leaching of the radioactive element from the electroplated layer, but it is preferable that the polymer layer reduce the leaching of the radioactive element from the radioactive electroplated substrate to a suitable level. For example, if a substrate is electroplated with radioactive iodine, then following the coating with a polymer, a suitable level of leaching is below about 120 $\mu$Ci with dry swabs (average of 6 swabs).

The radioactive, electroplated substrate coated with a polymer layer is also sealed in a jacket layer. By the term 'jacket layer' it is meant a bio-compatible material which encapsulates the radioactive, electroplated and polymer coated substrate. Typically the electroplated, polymer coated substrate is introduced within the jacket layer, and the jacket sealed to ensure little or no leaching of the isotope from the coated substrate. Preferably, the jacket layer is of a polymer is composition, which may be the same or different from that of the polymer layer. For example, the jacket layer may comprise but is not limited to nylon, nylon-12, polyurethane, thermoplastic polyurethane, high density polyethylene, thermoplastic elastomers, thermoplastic olefin, polybutylene terephtalate, polyethylene, ethylene-propylene terpolymer rubber and any combination thereof. The jacket layer maybe pre-formed and the electroplated, polymer coated substrate is inserted into the jacket layer which is then sealed. For example which is not to be considered limiting, the medical device may be a wire, and the jacket layer may be a tube that is dimensioned to slip over the electroplate, polymer coated wire. However, it is also contemplated that the jacket layer may be applied in a liquid form, in an analogous manner as the firstpolyrner layer, or that the jacket layer of desired dimension is extruded directly around the electroplated, polymer coated substrate and sealed. If applied in liquid form, the liquid jacket solution is of a much greater consistency than that used for the first polymer coating.

Preferably, the jacket layer does not substantially attenuate radiation emitted from the radioactive, electroplated substrate. Also, it is preferable that the jacket layer does not impart excessive bulk to the electroplated substrate so that the jacket layer does not significantly alter the properties of the substrate when sealed. For example, but not wishing to be limiting, a pliable substrate should remain pliable following electroplating, polymer coating and sealing within a jacket layer.

The jacket layer of the radioactive medical device of the present invention acts to protect the radioactive, electroplated, polymer coated substrate, and also serves as a barrier to reduce leaching of the radioactive element from the electroplated substrate. When coated within the jacket layer, the amount of leaching of the radioactive isotope from the substrate is at or below to a specific level as required for the radioactive medical device. For example, which should not be considered limiting in any manner, it is preferred that the jacket layer reduces the leaching of radioactivity from a medical device to be implanted within an animal to about 5 nCi or lower, as per ANSI standards (International Organization for Standardization (ISO) 9978-1992 (E) "Radiation Protection-sealed Radioactive Sources-Leakage Test Methods" Section 5).

Below is described the preparation of a medical device that is electroplated using a volatile radioactive isotope and coated as described herein. However, it is to be understood that the procedure described exemplifies the use of a substrate, isotope, and coating compositions that may be used to produce a coated medical device produced according to the methods of the present invention, and should not be used to limit the invention in any manner. In this example, the electroplating process is performed using an aqueous solution of sodium iodide, the silver wire as the anode and a platinum wire as the cathode. The pH of the solution is preferably alkaline, more preferably at a pH of about 10 or greater. Without wishing to be bound by theory, it is thought that the platinum wire acts as an inert conductor and does not participate in the redox chemistry of the electroplating process except as a conductor of electrons for the chemical reactions. The half reactions of the process may be as follows:

| | $E^\circ$ (V) |
|---|---|
| Half Reactions | |
| $Ag(s) + I^-(aq) \longleftrightarrow AgI(s) + 1\ \acute{e}$ | 0.152 |
| $Ag(s) \longleftrightarrow Ag^+ + 1\ \acute{e}$ | −0.799 |
| $O_2 + 2\ H_2O + 4\ \acute{e} \longleftrightarrow 4\ OH^-$ | 0.401 |
| Reaction | |
| $4Ag(s) + 2\ H_2O + 2\ NaI + O_2 \longleftrightarrow 2\ AgI(s) +$ | −0.246 |
| $2\ Ag(OH) + 2\ NaOH$ | |
| or | |
| Half Reactions | |
| $Ag(s) \longleftrightarrow Ag^+ + 1\ \acute{e}$ | −0.799 |
| $O_2 + 2\ H_2O + 4\ \acute{e} \longleftrightarrow 4\ OH^-$ | 0.401 |
| Reaction | |
| $4\ Ag(s) + 2\ H_2O + 2\ NaI + O_2 \longleftrightarrow 2\ AgI(s) + 4\ NaOH$ | −0.398 |

According to the half reactions shown above, the electrical potential for electroplating a silver wire with iodine is negative, suggesting that the electroplating reaction is not spontaneous and a voltage is applied for the reaction to occur. Without wishing to be limiting and bound by theory, the magnitude of the voltage required to effect an electroplating process depends on the metal present in the substrate and the radioactive element being electroplated onto the substrate as well as other factors. Also evident to someone of skill in the art is that a current is used to drive the electroplating process. Preferably, a current of about 15 $\mu$A to about 20 $\mu$A is applied for a period of about 2 hours to electroplate the silver wire with iodine-125.

To estimate the quantity of iodine electroplated onto a silver wire, the mass of each wire may be measured prior to and after electroplating. Under a first set of conditions, it was noted that the concentration of NaI in the electroplating solution affected the efficiency of the electroplating reaction.

Changing the concentration of NaI in the electroplating solution from 1 µg/mL to 20 µg/mL resulted in a colour change in the platings from dark grey to golden yellow, and had an impact on the efficiency of the electroplating reaction. Similarly, it was noted that wires that were not properly cleaned also affected the efficiency of the electroplating reaction. Thus, it is preferable that the substrates are thoroughly cleaned prior to being electroplated. However, it is noted that wide variation in the concentration of NaI could be used to effectively electroplate silver wires and other metallic objects. The efficiency of platings under different conditions is shown in Table 1:

TABLE 1

Electroplating Conditions

| Test # | I plated (mg) | Duration (hrs) | pH | Potential (initial) | Potential (final) | Current (mA) |
| --- | --- | --- | --- | --- | --- | --- |
| 1 | 100 | 1 | n.d. | — | 136.9 | 20 |
| 2 | 180 | 2 | n.d. | 258 | 299 | 20 |
| 3 | 290 | 3 | n.d. | 303 | 308 | 20 |
| 4 | 160 | 1.5 | n.d. | 660 | 1001 | 30 |
| 5 | 170 | 2 | n.d. | 461 | 487 | 15 |
| 6 | 130 | 1.5 | 7.45 | 443 | 463 | 20 |
| 7 | 150 | 2 | 10.2 | 470 | 814 | 20 |
| 8 | 230 | 2 | 11 | 438 | 532 | 20 | n.d. not determined

Table 1 illustrates that there is a wide variation in the conditions which allow efficient electroplating. For example, efficient electroplating was observed after different time periods and pH conditions of the electroplating solution. In addition, the electroplating reaction could be performed under a wide variety of voltages and currents.

In addition to the conditions described in Table 1, it was also observed that changing the volume of the electroplating solution, altering the depth of submersion of the silver wire (the anode) and the platinum wire (the cathode) and changing the distance between the anode and cathode in the electroplating solution also affected the efficiency of the electroplating reaction.

Figure 3:
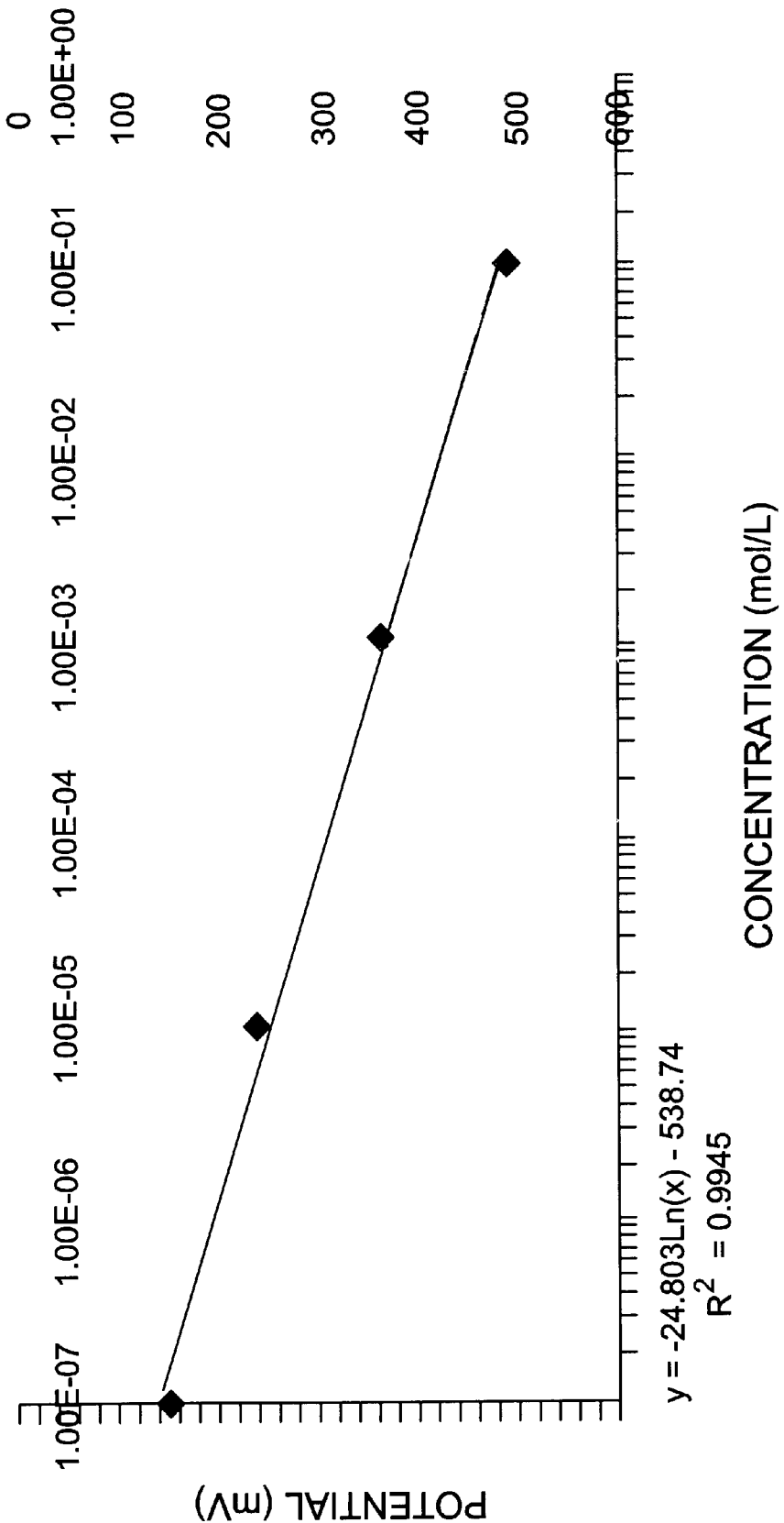
FIG. 3 depicts a graph of ion potential versus the concentration of ion in an electroplating solution.

To further evaluate the amount of iodine that can be electroplated onto a silver wire, numerous wires were electroplated with iodine and the ion potential of the NaI solution was measured before and immediately after electroplating using a iodine specific electrode. The purpose of these experiments was to ensure that the difference in the ion concentrations prior to and after electroplating corresponds to the mass of iodine electroplated on the wire. Using standard NaI solutions from $1.00 \times 10^{-1}$ to $1.00 \times 10^{-7}$ M, ion potential versus concentration plots were plotted for the purpose of determining the concentration of iodine in solution before and after electroplating and estimating the amount mass of the radioactive element on the wire. FIG. 3 shows a typical ion potential versus concentration plot. The mass of iodine on the wire calculated as the difference of the ion potential of the electroplating solution before and after electroplating, was within about 12% of the mass of iodine measured by weighing the wire. Thus, the mass of a radioactive electroplated layer of substrate may be determined by measuring the change in the radioactivity of the electroplating solution prior to and after electroplating.

In an aspect of an embodiment of the present invention, silver wires were electroplated with a NaI solution containing trace amounts of iodine-125. The electroplating process and conditions were performed as described in the Examples section, except that trace levels of I-125 were used in the electroplating reaction. It was noted that about 43% of the I-125 radioactivity in solution could be electroplated onto a substrate using the conditions described in the examples herein. Thus, in subsequent electroplating trials, a solution comprising about 7 Ci of I-125 is used to electroplate about 3 Ci of radioactive iodine-125 onto the substrate. However, someone of skill in the art will understand that higher or lesser amounts of radioactivity may be used to electroplated higher or lower amounts of radioactivity onto a substrate if other conditions of the electroplating solution are altered.

In a preferred embodiment, about 3 to about 5 Ci of iodine-125 (comprising about 0.173 mg iodine-125 of specific activity of about 17.27 Ci/mg) is coated on a silver wire having a diameter of about 0.25 mm, and a length of about 3 cm. This represents about a 54-fold increase in loading of I-125 compared to substrates of the prior art. For example, the current state of the art loading for I-125 onto a silver wire is approximately 5.5 mCi per 3 mm length of a 0.5 mm diameter wire (Mediphysics/Amersham Model 6711). However, higher or lower levels of radioactive iodine-125 can also be electroplated onto a substrate by varying the conditions of the electroplating reaction. For example, conditions which may affect the amount of radioactivity deposited or the rate at which the radioactivity is deposited may include, but are not limited to, the amount of radioactive material in an electroplating solution, the specific activity of the radioactive material in an electroplating solution, the voltage of the electroplating reaction, the current of the electroplating reaction, the time period of the electroplating process, the characteristics of the substrate, the affinity of the radioactive element in the electroplating solution for the substrate or a combination thereof.

The electroplating method for affixing radioactive elements onto a substrate as described herein, permits uniform coverage of the substrate with a radioactive element and provides a predictable radiation field at a given distance from the device. However, variations are contemplated to electroplate substrates other than silver and also substrates other than wires. One of skill in the art will appreciate that the half reactions, current, voltage and time of electroplating will vary depending on the type of material acting as the substrate in the electroplating reaction, as well as the nature of the material being deposited on to the substrate. For example, but not wishing to be limiting the electroplating method allows a number of wires, medical devices and sources to be made radioactive using radioactive elements such as but not wishing to be limiting P-32, S-35, Cl-36, Sc-47, Cu-67, Y-90, Mo-99, Pd-103, Sn-117m, I-123, I-124, I-125, I-129, I-131, Ce-144, Ho-166, Re-186, Re-188, W-188, Ir-192, and Au-199. The radioactive element may be selected based on the radiation dose required to be delivered to diseased tissue within a patient. For example, it is well known in the art that different radioactive elements decay with different radiation energies, or different particles than other radioisotopes. Alternatively, the radioactive element may be selected based on the time for the radioactive element to decay. For example, it is well known in the art that certain radioactive elements have decay halftimes that vary widely. Thus, in some situations it may be advantageous to use a radioactive medical device according to the present invention which comprises a radioactive element which decays quickly in time. Conversely, in some situations it may be advantageous to use a radioactive medical device according to the present invention which decays slowly in time.

After the substrate of the radioactive medical device of the present invention is electroplated with a layer of radioactive material, the substrate is coated with a first polymer layer. Prior to coating the wire with the first polymer layer, the substrate is preferably rinsed to remove residual radioactivity that may have not been properly electroplated onto the substrate and dried. Preferably, the radioactive, electroplated substrate is coated with one to about ten layers of polymer depending upon the thickness, solids concentration or density of the polymer solution. An example of a polymer is polyurethane. Preferably the polymer is polyurethane PU-EG65D. Each layer of polyurethane is preferably allowed to cure before the next layer of polyurethane is applied to the radioactive, electroplated substrate. In a preferred embodiment, the radioactive, electroplated substrate is coated with five layers of polymer comprising about 6% w/v polyurethane in methylene chloride, at a temperature of about 40° C. The layers of polymer may be applied by any method known in the art. For example, but not meant to be limiting, the electroplated substrate may be dipped in a polymer solution. The substrate is preferably allowed to air dry overnight to ensure that the polymer coating has properly cured. Using this method, the coating a radioactive, electroplated wire of length 3 cm and diameter 0.25 mm with five layers of polyurethane polymer increases the diameter of the wire to about 0.35 mm.

After the first polymer coating is complete, the electroplated, polymer coated substrate coated substrate may be tested to determine the amount of leaching of the radioactive element from the electroplated layer. The test may be, but is not limited to a swab test, an immersion test, a snif test, or a combination thereof (see Example 6), however, other test may also be used as required. The leaching test may comprise a dry swipe test, wet swipe test. If the radioactive, electroplated substrate comprises I-123, I-124, I-125, I-129, I-131 or a combination thereof, it is preferable that a dry swipe test is used to measure leaching. However, for other radioactive elements, a wet swipe test may be preferable. In the case of a I-125 coated wire, coated with the first polymer coating, each tests indicate that about 70 $\mu$Ci leach from the coated substrate surface.

After the radioactive, electroplated substrate is coated with the first polymer, the radioactive medical device is sealed in a jacket layer. The jacket layer further reduces the leaching of the radioactive isotope from the radioactive medical device of the present invention to below about 5 nCi as set by ANSI standards. For example which is not meant to be limiting, a radioactive, electroplated substrate, coated with a first polymer may be inserted into a nylon sleeve and the open end of the sleeve capped with a nylon plug and a biomedical UV cured glue may be used to seal the end of the nylon tubing.

The jacketed substrate is tested using the methods outlined in Example 6 to ensure that leaching of the radioactive element from the electroplated substrate is below a level of about 5 nCi. For example, a leach test may comprise a snif test wherein any potentially volatile radioactive elements that may leach from the radioactive, electroplated substrate coated with at least one layer of polymer and sealed in a jacket layer may be trapped on a carbon disc, which is subsequently analysed for radioactivity. Preferably, this test is performed when the radioactive element of the radioactive, electroplated substrate is potentially volatile, such as but not limited to iodine. An alternate leach test may comprise an immersion test wherein the electroplated, polymer coated and jacketed substrate is immersed in a solution of a specific temperature for a specific time period. The temperature of the solution maybe about room temperature or greater and the time period may as little as a few seconds to as long as about 24 hours, but may depend on the specificity of the radioactive element being tested for leaching. In a preferred embodiment the solution is water. Preferably this test is performed in water for a period of about 24 hours and at about 25° C. Following the immersion period, an aliquot of the solution is measured for radioactivity using methods well-known in the art. In each of the three tests described, the leachate is preferably below 5 nCi for an implanted medical device. However, a different levels may be selected for different applications.

According to an embodiment of the present invention, five silver wire substrates were each electroplated with about 3 Curies ofradioactive I-125. After the wire substrates were electroplated with iodine-1 25, the wire substrates were coated with five coats of 6% (w/v) polyurethane (PU EG-65D) in dichloromethane. Each wire was tested for leaching of iodine-125 through the polyurethane coating by rubbing at least six dry swabs along the length of the wire substrate and determining the average radioactivity in all the swabs. As is shown in Table 2, five coats of polyurethane reduced leaching of radioactive iodine to between about 0.1 and about 64 $\mu$Ci when assayed using the dry swab test described above. These electroplated and coated wires are suitable for sealing within a jacket layer comprising, for example nylon 6—6. In Table 2 it is noted that each of the radioactive medical devices of the present invention shows less leaching than the 5 nCi level set by ANSI standards, when assayed by a dry swab leaching test and an immersion leaching test as performed as described in Example 6.

TABLE 2

Leach tests of electroplated wire with a first polymer layer (Coated wire), or a first and second (jacket) layer (sealed wire).

| wire | Activity plated onto wire (Ci) | Coating | Coated Wire Leach test* ($\mu$Ci) | Sealed Wire Leech Test* ($\mu$Ci) | Immersion Leech Test ($\mu$Ci) |
|---|---|---|---|---|---|
| W11 | 3.26 | PU EG-65D | 11 | 0.01 | 0.9 |
| W12 | 3.18 | PU EG-65D | 0.78 | 0.19 | 0.8 |
| W23 | 3.02 | PU EG-65D | 66 | 0.05 | 0.8 |
| W24 | 3 | PU EG-65D | 0.13 | 1.7 | 4.1 |

*dry swab test

Figure 4:
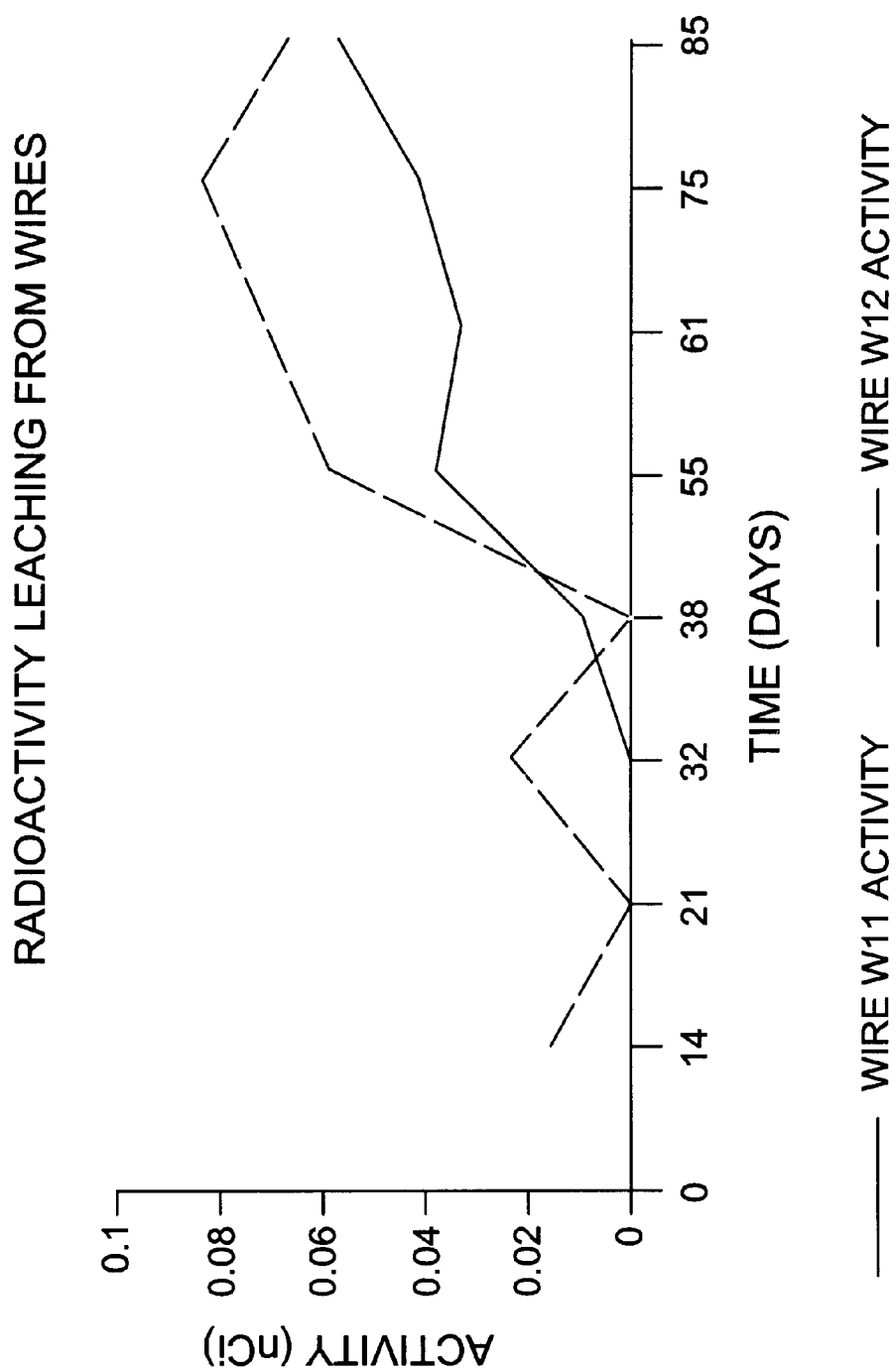
FIG. 4 shows radioactive iodine leaching from an embodiment of the present invention comprising a radioactive, electroplated substrate coated with at least one layer of polymer and sealed in jacket layer.

Referring now to FIG. 4, two radioactive medical devices of the present invention were tested for leaching over an extended period of time. FIG. 4 shows leaching of iodine-125 from a radioactive, electroplated substrate coated with five layers of polyurethane and sealed in ajacket layer of nylon 6—6 according to an embodiment of the present invention over a period of 85 days from the time of sealing the polymer-coated radioactive source in a jacket layer. Both radioactive medical devices exhibit a relatively small increase in radioactive element leaching, but the radioactive leaching appears to be well within acceptable limits. The results suggest that the a first polymer and a second jacket layer reduce leaching of the radioactive element disposed on the radioactive, electroplated layer of the substrate of the radioactive medical device of the present invention to a level below about 5 nCi.

The longitudinal uniformity of the radioactive layer on the radioactive, electroplated susbtrate coated with a least one layer of polymer and sealed in a jacket layer may be determined by any technique known in the art, for example, but not limited to gafchromic film dosimetry, wire scanning or a combination thereof. Preferably, the deviation in the longitudinal uniformity of the radioactive layer is less than about +25%, more preferably less than about +20% and still more preferably, less than about +20%. In addition, the longitudinal uniformity of the radioactive layer disposed on the substrate of the radioactive device of the present invention may be optionally determined following coating with at least one layer of polymer but before sealing in a jacket layer.

Figure 5:
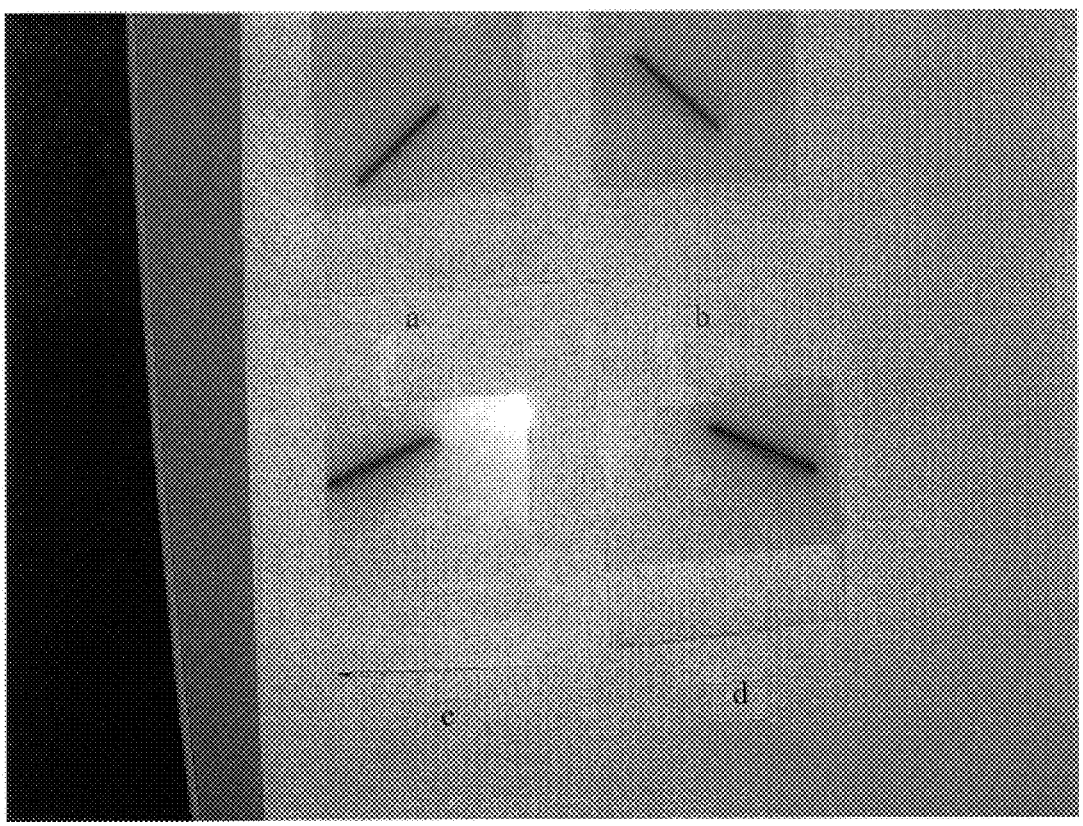
FIG. 5 shows representative examples of radiographic films used for gafchromic film densitometry of a radioactive medical device of the present invention.

Four radioactive medical devices of the present invention were examined to determine the longitudinal uniformity of the radioactive layer disposed thereon. Each of the four electroplated, coated and sealed wires was tested by gafchromic film dosimetry or wire scanning. Gafchromic dosimetry may be performed by making a 'sandwich' of the sealed source between two pieces of appropriate radiographic film. Radioactivity emitted from the radioactive medical device of the present invention interacts with the radiographic films. In order to quantify the amount of radioactivity that is emitted from the source, a number of different substrates emitting different known amounts of radioactivity are placed in contact with radiographic film for a fixed period. The film is developed and the regions, which appear as dark bands are quantified using computerized densitometry as is know within the art. A representative example of a radioactive film developed after gafchromic film dosimetry is shown in FIG. 5 The results of gafchromic film dosimetry for four radioactive medical devices of the present invention are shown in Table 3:

TABLE 3

Uniformity of coating

| Wire | Length of wire (mm) | Top film Average Abs. | Bottom Film Average Abs. | (Gy) |
| --- | --- | --- | --- | --- |
| W11 | 27.5 | 1.23 | 1.03 | 18.07 |
| W12 | 29.5 | 0.93 | 1.19 | 16.72 |
| W23 | 28 | 1.1 | 1.03 | 16.79 |
| W24 | 30 | 0.68 | 0.93 | 11.82 |

Figure 6:
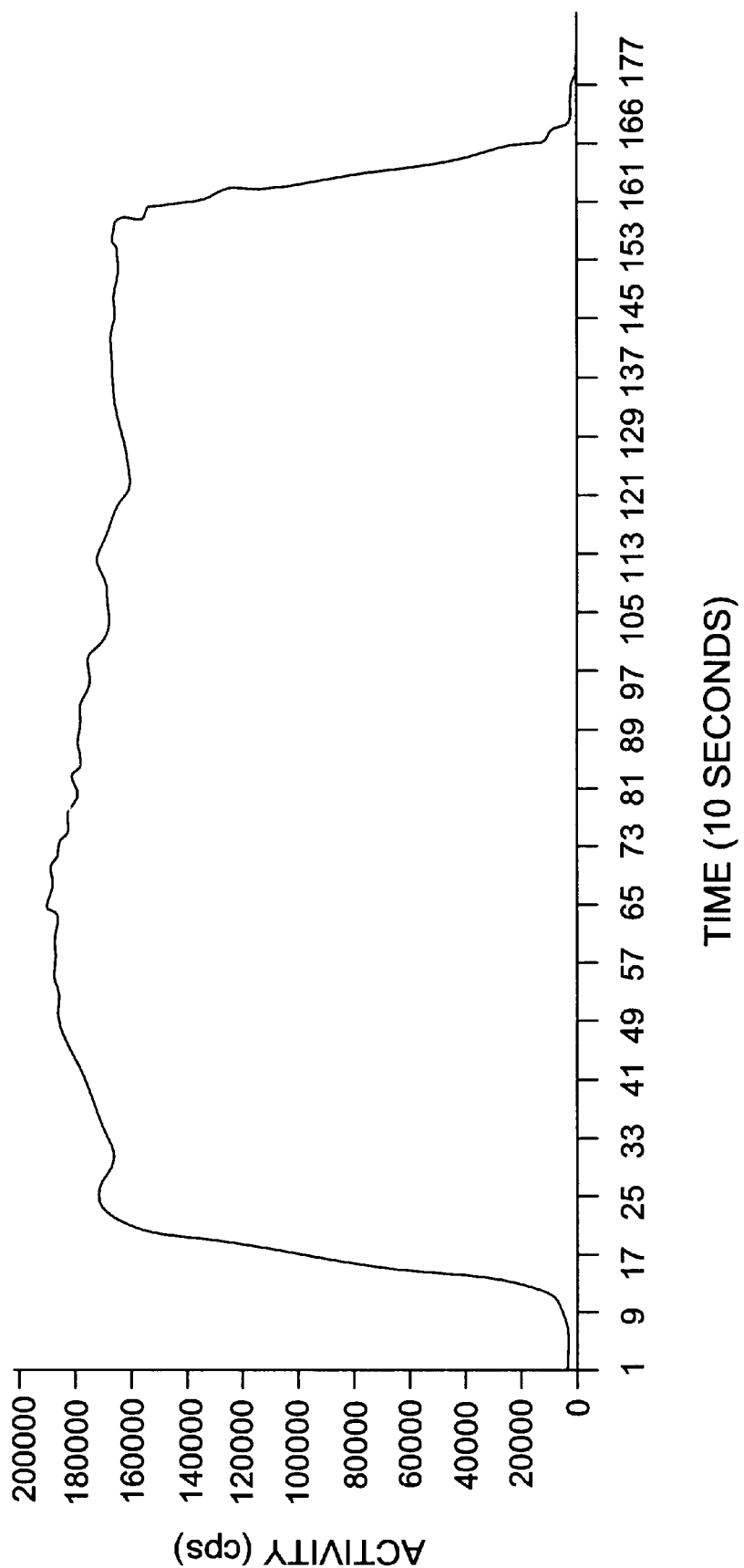
FIG. 6 shows a radioactive scan of a radioactive medical device of the present invention.

A radioactive scan of one of the radioactive medical devices of the present invention is shown in FIG. 6. Collectively, FIGS. 5, 6 and Table 3 suggest that radioactive layers of the radioactive medical devices of the present inventions are uniform over their length and uniform over their circumference.

The radioactive medical devices contemplated by the present invention provide numerous advantages over radioactive medical devices known in the prior art. For example, most of the prior art medical devices describe radioactive substrates or coating procedures wherein up to 300 mCi of a radioactive ion can be incorporated into or onto a substrate. In contrast, the present invention allows relatively large amounts (in the range of 3 to 5 curies or higher) of radioactive iodine, or other radioactive element to be uniformly electroplated onto a wire or other substrate. In addition, the subject matter of the current invention also demonstrates that a radioactive, electroplated substrate can be coated with a polymer and sealed in a jacket layer to provide a barrier against leaching of the radioactive element from the substrate without significant attenuation of the radioactivity of the substrate. Coating a radioactive, electroplated as described herein exhibits several other advantages over other coatings known in the art, including that it is inexpensive and more easily performed than applying other coatings such as titanium, or gold. Also, the coatings as described herein do not impart significant rigidity to the substrate, and may allow a substrate, for example a wire, to remain pliable and shaped as desired.

The radioactive medical device of the present invention may be used as a stent, wire or seed, for example as described in U.S. Pat. No. 4,323,055, U.S. Pat. No. 3,51,049, U.S. Pat. No. 5,713,828, U.S. Pat. No. 5,163,896, U.S. Pat. No. 5,342,283, for brachytherapy, restenosis, or in applications where it is desirable to deliver radiation to diseased tissue. However, the use of the radioactive medical device is not limited to these specific areas or applications.

The above description is not intended to limit the claimed invention in any manner, furthermore, the discussed combination of features might no be absolutely necessary for the inventive solution.

The present invention will be further illustrated in the following examples. However, it is to be understood that these examples are for illustrative purposes only, and should not be used to limit the scope of the present invention in any manner.

EXAMPLE 1

Preparation of a Substrate to be Electroplated

A substrate comprising a silver wire (LS188374) of 95 mm length and 0.25 mm diameter is washed by brushing lightly using with a tooth brush containing medium bristles and a small amount of cleanser (Aim Gel containing 0.23% w/w NaF). Following washing, the wire is gently wiped, placed in a beaker and rinsed three times with distilled-deionized water. Following this washing procedure, the wire is straightened on a clean flat surface. A length of 66 mm on the wire is measured and is gripped at this location using disposable tweezers. While tightly holding the wire, the upper portion of the wire (approximately 25 mm) is bent to create a "detour" in the wire (the detour usually comprises two right-angle bends in the wire and facilitates coating the proper length of wire). A disposable pipette is subsequently used to rinse the silver wire and the silver wire is allowed to air dry. While holding the wire with disposable tweezers, the end of the wire is dipped 1–2 mm into a polymer solution comprising 6% (w/v) polyurethane so that the end of the wire is not plated with radioactivity. The wire is re-dipped two additional times. Following the final dipping, the wire is gently touched to the meniscus of the polymer solution. The wire is subsequently allowed to air dry for a minimum of 60 minutes.

EXAMPLE 2

Radioactive Electroplating of the Substrate

The protocol described below involves the use of high levels of radioisotopes and must be performed by qualified personnel in an appropriate radioactive containment facility. In addition, other safety measures which pertain to the use of $I^{125}$ must be observed.

An electroplating solution containing 20 ml dilute NaOH and 7Ci $NaI^{125}$, pH approximately 11.0 is placed in a scintillation vial with a small stir-bar. The septum from an EPA vial cap is removed and using a rotary tool, the threading in the cap is ground out so that the cap can be placed onto the vial snugly, ensuring that one thread towards the inner part of the cap remains to hold the septum. While wearing a rubber glove, a 25 mm length of Teflon® tubing (Outer diameter:0.065", Inner Diameter:0.030"). Using an 18G needle, a straight hole approximately 2.5 mm from the edge of the EPA vial septum is made, and a similar hole is made for insertion of the platinum wire. A 21G×1.5" needle is slid into the teflon tubing and the needle and teflon are inserted into the septum 10 mm across from the other puncture site. The Teflon® tube is inserted such that it protrudes 17 mm from the septum. Subsequently, a 50 mm platinum wire is inserted into the hole such that the 21 mm portion protrudes from the septum. Using tweezers, the long end of the silver wire is inserted into the Teflon® tube and is dropped into. The vial cap assembly is connected to a dummyvial filled with 20 mL of distilled/deionized water and the edge of the cap is taped to securely fasten the vial to the assembly ensuring that the silver wire is suspended 28–30 mm into the electroplating liquid and that the platinum wire is suspended 10 mm into the electroplating liquid.

EXAMPLE 3

Electroplating Conditions

The vial containing the $NaI^{125}$ electroplating solution is gently mixed and the total radioactivity in a Capintec dose calibrator. This measurement provides an indication of the radioactive activity of the vial prior to plating. The vial is clamped onto a stand and alligator clips are connected to silver (Ag) and platinum (Pt) wires with the Ag wire connected to the positive terminal (cathode). Electroplating is carried out for 2 hours using a current of 20 $\mu$A and a potential difference between 200 and 600 mV. The potential difference is monitored every 15 minutes over the course of the reaction. Following the electroplating reaction, the radioactivity in the vial is re-measured in the Capintec dose calibrator. The radioactive, electroplated substrate is then allowed to dry behind shielding for 1hr. The wire is removed by pulling it through the Teflon® tube from below to prevent the Teflon® from scraping the plating. Following the electroplating process, the radioactive, electroplated substrate is dipped into a test tube containing water.

EXAMPLE 4

Coating the Radioactive, Electroplated Substrate With a First Polymer Layer In a scintillation vial 0.9 g of EG65D tecoflex polyurethane beads and methylene chloride are added such that the total mass in each of the scintillation vials is 15.0 g (6% w/v polyurethane beads in methylene chloride). The mixture corresponds roughly to a 3 cm height in the vial and 15 ml volume for each scintillation vial. The solutions are stirred with gentle heating until the polyurethane solution is homogeneous. The solution is transferred to five 10×75 mm test tubes and the tubes are capped tightly. The tubes are placed in a block heater at 40° C. The electroplated radioactive wire is dipped into the first tube of polyurethane solution and then dried for at least 1 hr. After drying, the dipping procedure is repeated four additional times, each with a new tube containing the polyurethane mix. To quantify leaching of radioactive iodine from the electroplated wire into the polyurethane dipping tubes, the activity of each tube is measured in a Capintec dose calibrator.

EXAMPLE 5

Sealing the Radioactive, Electroplated Substrate Having at Least on Polymer Coating in a Jacket Layer.

The radioactive, electroplated substrate coated with at least one layer of polymer is sealed in a nylonjacket comprising nylon 6—6 having an outer diameter of about 0.030" and an outer diameter of about 0.018".

EXAMPLE 6

Leaching Tests

Swab Test

Wet swab tests were also used to verify that the leach rate of radioactive iodine was within acceptable levels. Briefly, a series of 5 swabs were moistened with water and swiped along each side of the wire. The procedure was repeated for each of the four remaining swabs and the radioactivity of each swab was measured against a blank swab. Dry swab tests are performed in an identical manner except that the swab is not moistened prior to being swiped along each side of the wire.

Immersion test

The radioactive, electroplated wire coated with at least one layer of polymer and sealed in a jacket layer is placed in a test tube comprising water and is maintained at a temperature of 20–25° C. (room temperature) for 24 hours. Following the 4 hour incubation, the wire is removed, and the water measured for any leaching of radioactive iodine in a Capintec dose calibrator.

Snif Test

The Snif test is performed by gentle air suction through a carbon-disc filter and subsequently measuring the radioactivity in an appropriate radioactive detector device.

EXAMPLE 7

Gafchromic Film Dosimetry and Radioactive Substrate Scanning

Gafchromic Film Dosimetry

Gafchromic film dosimetry of the radioactive, electroplated wire coated with five layers of polyurethane and sealed in a jacket layer is performed using Gafchromic film analysis (Chiu-Tsao, S. T., de la Zerda, A., Lin, J., and Kim, J. H. "High Sensitivity Gafchromic Film Dosimetry for $^{125}I$ seed." Med. Phys. 21, 651–657 (1994) which is herein incorporated by reference). A sheet of gafchromic film (Gafchromic Dosimetry Media, Type MD-55) is cut into four pieces. A piece of the film is inserted into a plastic business card pocket and each pocket is taped to the inside of a lucite block. The wire substrate is sandwiched between the two pieces of film. The film is exposed for a period between 10 and 30 minutes, developed and analyzed using computerized densitometry. Results suggest that the deposition of radioactive iodine on the wire is uniform over its length and circumference.

Radioactive Substrate Scanning

The uniformity of the radioactive coating is examined by scanning the length of the wire. The wire is placed in a crimp tube and a piece of stainless steel is placed over the scanner's detector.

All references are herein incorporated by reference.

The present invention has been described with regard to preferred embodiments. However, it will be obvious to persons skilled in the art that a number of variations and modifications can be made without departing from the scope of the invention as described herein.

The embodiments of the invention in which an exclusive property of privilege is claimed are defined as follows:

1. A radioactive medical device comprising a radioactive, electroplated substrate coated with at least one layer of polymer and sealed with a nonmetallic jacket layer, wherein the amount of radioactivity per unit area of said radioactive, electroplated substrate is from about 100 $mCi/mm^2$ to about 200 $mCi/mm^2$.

2. The radioactive medical device of claim 1 wherein said substrate is metal.

3. The radioactive medical device of claim 2 wherein said substrate is silver.

4. The radioactive medical device of claim 3 wherein said substrate is a wire.

5. The radioactive medical device of claim 1 wherein the radioactive, electroplated substrate comprises a radioactive element selected from the group consisting of P-32, S-35, CI-36, Sc-47, Cu-67, Y-90, Mo-99, Pd-103, Sn-117m, I-123, I-124, I-125, I-129, I-131, Ce-144, Ho-166, Re-186, Re-188, W-188, Ir-192, and Au-199.

6. The radioactive medical device of claim 1 wherein said at least one layer of polymer comprises from 1 to about 10 layers of polymer.

7. The radioactive medical device of claim 6 wherein said polymer comprises a compound selected from the group consisting of polyurethane, polypropylene, polysulfone, polyphenylsulfone, polyethersulfone, polyimide, nylon, polyester/polyolefins, ceramics, PVP, cellulose ester, polyglycolide, polylactic, nylon 6/6, polyethylene glycol, polyvinylidene fluoride and epoxy, or a combination thereof.

8. The radioactive medical device of claim 7 wherein said polymer is a polyurethane polymer.

9. The radioactive medical device of claim 8 wherein said polyurethane polymer is polyurethane EG-65D.

10. The radioactive medical device of claim 1 wherein said non-metallic jacket layer comprises nylon, polyethylene, or polyurethane.

11. The radioactive medical device of claim 1, wherein said device is a stent.

12. The radioactive medical device of claim 1, wherein said device is a seed.

13. A method of radiation therapy comprising, delivering the radioactive medical device of claim 1 to the site of diseased tissue.

14. The method of claim 13, wherein the diseased tissue is associated with brachytherapy.

15. The method of claim 13, wherein the diseased tissue is associated with restenosis.

16. A radioactive medical device comprising a silver wire substrate electroplated with radioactive iodine to form a radioactive, electroplated wire substrate, said radioactive, electroplated wire substrate coated with at lease one layer of polyurethane and sealed with a non-metallic jacket layer, wherein the amount of radioactivity per unit area of said radioactive, electroplated substrate is from about 100 mCi/mm$^2$ to about 200 mCi/mm$^2$.

17. A method of manufacturing a radioactive medical device comprising the steps of:
 a) electroplating a substrate with a radioactive element to form a radioactive, electroplated substrate, wherein the amount of radioactivity per unit area of said radioactive, electroplated substrate is from about 100 mCi/mm$^2$ to about 200 mCi/mm$^2$;
 b) coating the radioactive, electroplated substrate with at least one layer of polymer to form a radioactive, electroplated substrate coated with at least one layer of polymer; and
 c) sealing the radioactive, electroplated substrate coated with at least one layer of polymer in a jacket layer.

18. A method of manufacturing a radioactive medical device comprising the steps of:
 a) electroplating a substrate with a radioactive element to form a radioactive, electroplated substrate at a current of from about 10–100 μA;
 b) coating the radioactive, electroplated substrate with at least one layer of polymer to form a radioactive, electroplated substrate coated with at least one layer of polymer and;
 c) sealing the radioactive, electroplated substrate coated with at least one layer of polymer in a jacket layer.

19. The method of claim 18, wherein in said step of electroplating (step a), said current is from about 10 to 30 μA.

20. The method of claim 19, wherein in said step of electroplating (step a), said current is applied from about 1 to about 2 hours.

* * * * *

UNITED STATES PATENT AND TRADEMARK OFFICE
CERTIFICATE OF CORRECTION

PATENT NO. : 6,638,205 B1
DATED : October 28, 2003
INVENTOR(S) : Chan et al.

It is certified that error appears in the above-identified patent and that said Letters Patent is hereby corrected as shown below:

<u>Column 3,</u>
Line 62, insert the words -- synthetic rubber and rubber compositions sold under the trademark -- before the word "VITON"

<u>Column 17,</u>
Line 19, insert the words -- synthetic rubber and rubber compositions -- before the word "nylon"

Signed and Sealed this

Tenth Day of February, 2004

JON W. DUDAS
*Acting Director of the United States Patent and Trademark Office*